United States Patent
Park et al.

(10) Patent No.: US 11,904,039 B2
(45) Date of Patent: Feb. 20, 2024

(54) COSMETIC COMPOSITION FOR MAKEUP REMOVAL COMPRISING WATER-SOLUBLE SURFACTANT AND OIL-SOLUBLE SURFACTANT

(71) Applicant: AMOREPACIFIC CORPORATION, Seoul (KR)

(72) Inventors: Hyo Young Park, Yongin-si (KR); Hyun Ju Yu, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 742 days.

(21) Appl. No.: 17/043,548

(22) PCT Filed: Mar. 28, 2019

(86) PCT No.: PCT/KR2019/003632
§ 371 (c)(1),
(2) Date: Sep. 29, 2020

(87) PCT Pub. No.: WO2019/190220
PCT Pub. Date: Oct. 3, 2019

(65) Prior Publication Data
US 2021/0059916 A1    Mar. 4, 2021

(30) Foreign Application Priority Data

Mar. 30, 2018   (KR) .................. 10-2018-0037438
Mar. 22, 2019   (KR) .................. 10-2019-0032725

(51) Int. Cl.
*A61Q 1/00*     (2006.01)
*A61K 8/34*     (2006.01)
(Continued)

(52) U.S. Cl.
CPC ............ *A61K 8/345* (2013.01); *A61K 8/0212* (2013.01); *A61K 8/60* (2013.01); *A61K 8/86* (2013.01); *A61Q 1/14* (2013.01)

(58) Field of Classification Search
CPC ...................................... A61K 8/345
See application file for complete search history.

(56) References Cited

U.S. PATENT DOCUMENTS

| 2004/0136943 | A1 | 7/2004 | Tomokuni |
| 2006/0078525 | A1 | 4/2006 | Tomokuni |
| 2018/0360713 | A1* | 12/2018 | Jouy ...................... A61K 8/068 |

FOREIGN PATENT DOCUMENTS

| CN | 101563058 A | 10/2009 |
| CN | 102370587 A | 3/2012 |

(Continued)

OTHER PUBLICATIONS

International Search Report for PCT/KR2019/003632 dated Jul. 4, 2019 [PCT/ISA/210].
(Continued)

*Primary Examiner* — Necholus Ogden, Jr.
(74) *Attorney, Agent, or Firm* — Sughrue Mion, PLLC

(57) ABSTRACT

A cosmetic composition for makeup removal and its use for removing facial make-up are disclosed. The composition includes a water-soluble surfactant and an oil-soluble surfactant and. The composition, more specifically, includes, as an active ingredient, a mixture of a water-soluble surfactant having a hydrophile-lipophile balance (HLB) value of 13 or more and an oil-soluble surfactant having an HLB value of 12 or less. The composition can excellently remove makeup residues resulting from using a makeup product, can excellently improve the transparency of the composition, and is excellent in feeling of use on the skin.

8 Claims, 1 Drawing Sheet

(51) Int. Cl.
*A61K 8/60* (2006.01)
*A61Q 1/14* (2006.01)
*A61K 8/02* (2006.01)
*A61K 8/86* (2006.01)

(56) References Cited

FOREIGN PATENT DOCUMENTS

| | | | |
|---|---|---|---|
| EP | 2468842 A1 * | 6/2012 | ............. A61K 8/368 |
| JP | 2006-022061 A | 1/2006 | |
| JP | 2011-126809 A | 6/2011 | |
| JP | 2012-214404 A | 11/2012 | |
| JP | 2014-91734 A | 5/2014 | |
| KR | 10-2002-0037206 A | 5/2002 | |
| KR | 10-2003-0051972 A | 6/2003 | |
| KR | 10-0712255 B1 | 4/2007 | |
| KR | 10-2010-0014247 A | 2/2010 | |
| KR | 10-2012-0070513 A | 6/2012 | |
| KR | 10-2014-0015080 A | 2/2014 | |
| KR | 10-1507814 B1 | 4/2015 | |
| KR | 10-2015-0046994 A | 5/2015 | |
| WO | WO-2018154298 A1 * | 8/2018 | ............... A61K 8/00 |

OTHER PUBLICATIONS

Office Action dated Aug. 16, 2022 issued by the Chinese Patent Office in Chinese Application No. 201980023453.7.
Chinese Office Action dated Mar. 22, 2023 in Chinese Application No. 201980023453.7.

* cited by examiner

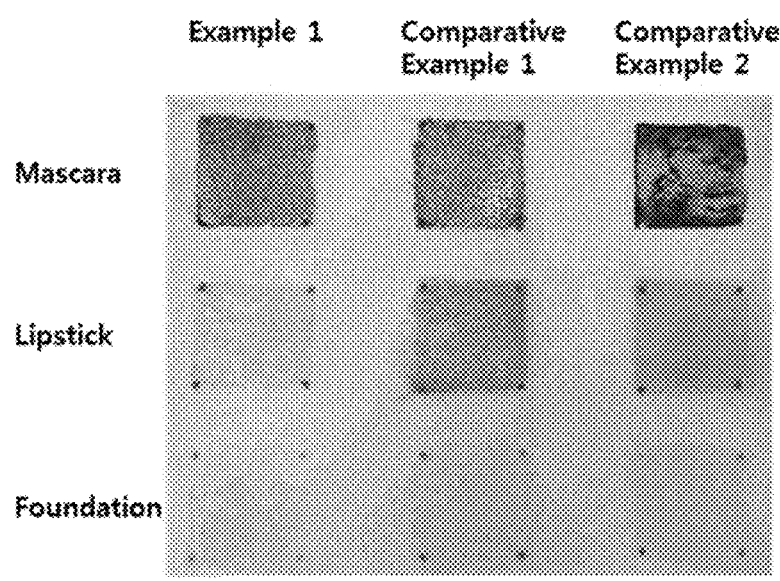

COSMETIC COMPOSITION FOR MAKEUP REMOVAL COMPRISING WATER-SOLUBLE SURFACTANT AND OIL-SOLUBLE SURFACTANT

CROSS REFERENCE TO RELATED APPLICATIONS

This application is a National Stage of International Application No. PCT/KR2019/003632 filed Mar. 28, 2019, claiming priority based on Korean Patent Application No. 10-2018-0037438 filed Mar. 30, 2018 and Korean Patent Application No. 10-2019-0032725 filed Mar. 22, 2019 the entire content of which is hereby incorporated by reference.

TECHNICAL FIELD

One aspect of the present disclosure relates to a cosmetic composition for makeup removal comprising a water-soluble surfactant and an oil-soluble surfactant and, more specifically, to a cosmetic composition for makeup removal which comprises, as an active ingredient, a mixture of a water-soluble surfactant having a hydrophile-lipophile balance (HLB) value of 13 or more and an oil-soluble surfactant having an HLB value of 12 or less, and which can excellently remove makeup residues resulting from using a makeup product, can excellently improve the transparency of the composition, and is excellent in feeling of use on the skin.

BACKGROUND ART

Various products are known as cleansing cosmetics that cleanse the skin. In general, cleansing products that remove color makeup ingredients are available in the form of cream, emulsion, liquid, and transparent gel according to their properties, and emulsion type, oil type, and aqueous type are available according to their types. Thus, they are used for various usages according to their characteristics.

As the emulsion type, cleansing lotions and creams are typical. They are characterized by imparting a cleansing effect by blending a large amount of oil with a nonionic surfactant. The emulsion type contains 20 to 70% by weight of the oily component, so it has an advantage that cleansing effect is excellent and softness and massage effects are excellent during use, but it has a disadvantage that since the amount of oil remaining on the skin after use is high, the oil has to wipe off with a tissue-off product if it is difficult to remove with water. In addition, there is a concern about skin irritation due to physical stimulation by tissue-off products. The oily feeling remains even after wiping off with the tissue, so there is an inconvenience that an aqueous face cleaning has to perform using a foam cleansing soap.

As a solution to the above-mentioned problems, Korean Unexamined Patent Application Publication No. 2003-0051972 discloses a cleansing composition containing a small amount of oil without a surfactant, and Korean Unexamined Patent Application Publication No. 2002-0037206 discloses a cleansing composition for removing oil-free type oil-in-water makeup components. However, in the case of the former, it is, actually, difficult to remove makeup sufficiently with only a small amount of oil, and in the case of the latter, there is a limit to removing makeup components other than silicone.

Research to develop cleansing cosmetics for effectively removing such makeup is actively underway, but the progress of developing cleansing cosmetics with minimal irritation and excellent cleansing power without requiring double facial cleansing is still incomplete.

In addition, in general, in order to prepare a stable oil-in-water emulsion using a conventional surfactant, it is necessary that the surfactant be adsorbed to an aqueous/oil phase interface to form a liquid crystal, and for this purpose, the HLB (Hydrophile Lipophile Balance) value of the surfactant to be used must be carefully adjusted depending on the polarity of the oil phase. Moreover, even when adjusting the HLB value, it is frequently necessary to select an appropriate emulsifier according to the structure of the oil, and thus, there are many difficulties in the selection.

Under these technical backgrounds, the present inventors have conducted an intensive research to develop a cosmetic composition capable of improving the transparency of the composition while exhibiting an excellent makeup removal (cleansing) effect, as compared with a conventional cosmetic composition for makeup removal containing only a water-soluble surfactant (hydrophilic surfactant) as a main ingredient, and as a result, have found that the cosmetic composition according to one aspect of the present disclosure comprising, as an active ingredient, a mixture of a water-soluble surfactant having a HLB value of 13 or more and an oil-soluble surfactant having an HLB value of 12 or less in a specific ratio, has excellent effects if removing (cleansing) makeup components remaining on the skin due to makeup, does not contain oil even while improving the transparency of the composition, and thus, provide a refreshing feeling and improves the feeling of use, thereby completing one aspect of the present disclosure.

PRIOR ART DOCUMENT

[Patent Document]
1. Korean Unexamined Patent Application Publication No. 2003-0051972 (published on Jun. 26, 2003)
1. Korean Unexamined Patent Application Publication No. 2002-0037206 (published on May 18, 2002)

DETAILED DESCRIPTION OF THE INVENTION

Technical Problem

It is an object of one aspect of the present disclosure to provide a cosmetic composition for makeup removal having excellent effect of removing makeup.

Technical Solution

In order to achieve the above object, one aspect of the present disclosure provides a cosmetic composition for makeup removal which comprises, as an active ingredient, a mixture of a water-soluble surfactant having a HLB value of 13 or more and an oil-soluble surfactant having an HLB value of 12 or less, preferably, a cosmetic composition for makeup removal which comprises, as an active ingredient, a mixture of a water-soluble surfactant having a HLB value of 13 or more and an oil-soluble surfactant having an HLB value of 12 or less in a weight ratio of preferably 3 to 20:0.1 to 3.3, more preferably 4 to 17:0.1 to 1.5, most preferably 4.5 to 8:0.2 to 1.3.

Another aspect of the present disclosure provides the use of a mixture of a water-soluble surfactant having a HLB value of 13 or more and an oil-soluble surfactant having an HLB value of 12 or less in the preparation of cosmetic compositions or cosmetic products for makeup removal, more precisely the use as a makeup remover.

Advantageous Effects

The cosmetic composition for makeup removal according to one aspect of the present disclosure comprises a mixture of a water-soluble surfactant having a HLB value of 13 or more and an oil-soluble surfactant having an HLB value of 12 or less in a specific ratio, whereby the removal power (cleansing power) for makeup products is excellent, the turbidity of the composition is maintained below 15 NTU, so the effect of improving the transparency of the cosmetic formulation is very excellent, and it does not contain oil and thus, looks fresh and does not require double removal (washing/cleansing), and due to the use of a small amount of surfactant, it gives less irritation to the skin and is excellent in feeling of use.

BRIEF DESCRIPTION OF THE DRAWINGS

FIG. 1 is a photograph showing an excellent makeup removal power, that is, a cleansing effect, of the cosmetic composition for makeup removal of Example 1 according to one aspect of the present disclosure.

DETAILED DESCRIPTION OF THE EMBODIMENTS

Unless otherwise defined, all technical and scientific terms used herein have the same meaning as commonly understood by one of ordinary skill in the art to which the present invention belongs. In general, the nomenclatures used herein are those well-known and commonly used in the art.

Hereinafter, embodiments of one aspect of the present disclosure will be described in detail.

In one aspect of the present disclosure, the term "about" used to express length, area, volume, time (period), concentration, capacity (content, etc.), temperature, humidity, pressure, etc. refers to a margin of up to 10% of the number or the numerical range indicated.

In one aspect, the present disclosure relates to a cosmetic composition for makeup removal which comprises, as an active ingredient, a mixture of a water-soluble surfactant having a HLB (hydrophile-lipophile balance) value of 13 or more and an oil-soluble surfactant having an HLB value of 12 or less.

The HLB value best represents the properties of a surfactant, and essentially determines the nature of the system. Generally, a surfactant having an HLB value of 1.5 to 3 is used as an antifoaming agent, a surfactant having an HLB value of 4 to 6 is used as a water-in-oil emulsifier (W/O emulsion), a surfactant having an HLB value of 7 to 9 is used as a wetting agent, and a surfactant having an HLB value of 8 to 18 is used as an oil-in-water emulsifier (O/W emulsion).

In one aspect of the present disclosure, the HLB value of the water-soluble surfactant is 13 or more, most preferably 14 to 18. If the HLB value is less than 13, not only the makeup removal power (cleansing power) and the effect of improving the transparency of the composition are slight, but also a water-soluble composition cannot be prepared.

In one aspect of the present disclosure, the water-soluble surfactant may be at least one selected from the group consisting of polyglyceryl-6 caprylate, polyglyceryl-10 laurate, PEG-6 caprylic/capric glycerides, PEG-7 glyceryl cocoate, polysorbate 20, and disodium cocoamphodiacetate, and preferably, a mixture of polyglyceryl-6 caprylate and polyglyceryl-10 laurate.

In one aspect of the present disclosure, the HLB value of the oil-soluble surfactant is 12 or less, more preferably 9 to 12, most preferably 10 to 12. When the HLB value exceeds 12, the makeup removal power (cleansing power) is reduced, and the effect of improving the transparency of the composition may be lowered.

In one aspect of the present disclosure, the oil-soluble surfactant may be at least one selected from the group consisting of polyglyceryl-10 diisostearate, polyglyceryl-2 laurate, polyglyceryl-2 sesquicaprylate, polyglyceryl-5 trioleate, polyglyceryl-10 dioleate, PEG-20 glyceryl triisostearate, PEG-8 isostearate, PEG-8 glyceryl isostearate, PEG-20 glyceryl isostearate, PEG-15 glyceryl isostearate, polysorbate 60 and polysorbate 80, and preferably, polyglyceryl-10 diisostearate.

In one aspect of the present disclosure, the composition may be prepared in an oil-in-water type (O/W emulsion) or a water-in-oil type (W/O emulsion), and is preferably prepared by an oil-in-water type emulsification method.

In one aspect of the present disclosure, improvement in transparency of the composition means a transparent or translucent state of the cosmetic formulation.

In one aspect of the present disclosure, the composition has a nephelometric turbidity unit (NTU) of 15 or less, preferably 13 or less, and most preferably 10 or less.

In one aspect of the present disclosure, the mixture is a mixture of a water-soluble surfactant and an oil-soluble surfactant in a weight ratio of preferably 3 to 20:0.1 to 3.3, more preferably 4 to 17:0.1 to 1.5, most preferably 4.5 to 8:0.2 to 1.3. When it is out of the above weight ratio, the makeup removal power (cleansing power) is reduced, and the transparency improving effect of the composition may be lowered.

In one aspect of the present disclosure, in the state where the weight ratio of the water-soluble surfactant and the oil-soluble surfactant is maintained, the content of the water-soluble surfactant contained in the composition may be 1 to 40% by weight, preferably 3 to 20% by weight, more preferably 4 to 17% by weight, most preferably 4.5 to 8% by weight based on the total weight of the composition. When the content of the water-soluble surfactant is less than 1% by weight based on the total weight of the composition, the makeup removal power (cleansing power) and the transparency improving effect of the composition, which are intended for use as cosmetics for makeup removal, are slight. When the content of the water-soluble surfactant exceeds 40% by weight, the increase in the effect is not large compared to the increase in the content, and formulation stability and feeling of use may be reduced.

In one aspect of the present disclosure, in the state where the weight ratio of the water-soluble surfactant and the oil-soluble surfactant is maintained, the content of the oil-soluble surfactant contained in the composition may be 0.1 to 10% by weight, preferably 0.1 to 3.3% by weight, more preferably 0.1 to 1.5% by weight, most preferably 0.2 to 1.3% by weight based on the total weight of the composition. When the content of the oil-soluble surfactant is less than 0.1% by weight based on the total weight of the composition, the makeup removal power (cleansing power) and the transparency improving effect of the composition, which are intended for use as cosmetics for makeup removal, is slight. When the content of the oil-soluble surfactant exceeds 10% by weight, the increase in the effect is not large compared to the increase in the content, and formulation stability and feeling of use may be reduced.

In one aspect of the present disclosure, the composition may, in consideration of the use restriction amount based on the rules concerning the safety of cosmetic products, further contain an adjuvant commonly used in the field of cosmetic or dermatology such as, moisturizers (polyol, etc.), oils, waxes, viscosity modifiers, thickeners, pH adjusters, fats, organic solvents, solubilizers, concentrates, gelling agents, softeners, antioxidants, suspending agents, stabilizers, foaming agents, perfumes, water, ionic emulsifiers, nonionic emulsifiers, fillers, sequestering agents, chelating agents, preservatives, vitamins, wetting agents, dyes, pigments, hydrophilic activators, lipophilic activators, lipid vesicle, or any other ingredient commonly used in cosmetic products. The composition of one aspect of the present disclosure may further contain skin absorption-enhancing materials in order to increase the effect of improving skin conditions.

In one aspect of the present disclosure, the composition is not particularly limited in formulating into dosage forms, but may be a cosmetic composition having a dosage form such as, softening lotion, astringent lotion, nourishing lotion, lotion, eye cream, nourishing cream, massage cream, cleansing cream, cleansing foam, cleansing water, powder, essence, and pack. The cosmetic composition of each of these formulations may contain various components that are blended in a conventional cosmetic composition depending on the various dosage forms described above or in compliance with the final purpose, and the type and amount of these components can be easily selected by those skilled in the art.

In one aspect of the present disclosure, the makeup may be produced by applying to the skin one or more cosmetic formulations selected from the group consisting of lipstick, lip gloss, lip balm, lip pencil, rouge, lip palette, pact, powder, blusher, twin cake, compact, powder pact, pressed powder, skin cover, foundation, concealer eyeshadow, eyebrow, eyeliner and mascara, but is not limited thereto.

Hereinafter, one aspect of the present disclosure will be described in more detail by way of examples. However, it would be obvious to those skilled in the art that these examples are for illustrative purposes only and the scope of one aspect of the present disclosure is not construed as being limited by these examples.

<Preparation of Cosmetic Composition for Makeup Removal>

The cosmetic compositions for makeup removal of Examples 1 to 7 and Comparative Examples 1 to 4 were prepared according to the compositions of Tables 1 and 2 below (unit: wt %).

TABLE 2

| Category | Material name | Comparative Example 1 | Comparative Example 2 | Comparative Example 3 | Comparative Example 4 |
|---|---|---|---|---|---|
| — | purified water | to 100 | to 100 | to 100 | to 100 |
| water-soluble surfactant | polyglyceryl-6 caprylate | 5 | 5 | 0 | 0 |
|  | polyglyceryl-10 laurate | 2 | 2 | 2 | 0 |
| oil-soluble surfactant | polyglyceryl-10 diisostearate | 0.05 | 0 | 1 | 1 |
|  | polyglyceryl-10 dioleate | — | — | — | — |

[Examples 1 to 7]: Cosmetic Composition Containing Water-Soluble Surfactant and Oil-Soluble Surfactant In order to prepare the cosmetic composition according to Examples 1 to 7 of Table 1, polyglyceryl-6 caprylate (HLB 15) and polyglyceryl-10 laurate (HLB 16) as water-soluble surfactants, and polyglyceryl-10 diisostearate (HLB 11) and polyglyceryl-10 diolate (HLB 11.7) as oil-soluble surfactants were used.

Specifically,

1) Respective mixtures were prepared by mixing according the following compositions: polyglyceryl-6 caprylate:polyglyceryl-10 laurate:polyglyceryl-10 diisostearate=weight ratio of 5:2:1 (see Example 1), polyglyceryl-6 caprylate:polyglyceryl-10 diisostearate=weight ratio of 7:1 (see Example 2), polyglyceryl-10 laurate:polyglyceryl-10 diisostearate=weight ratio of 7:1 (see Example 3), polyglyceryl-6 caprylate:polyglyceryl-10 laurate:polyglyceryl-10 diisostearate=weight ratio of 2:5:1 (see Example 4), polyglyceryl-6 caprylate:polyglyceryl-10 laurate:polyglyceryl-10 diolate=weight ratio of 5:2:1 (see Example 5), polyglyceryl-6 caprylate:polyglyceryl-10 laurate:polyglyceryl-10 diisostearate:polyglyceryl-10 diolate=weight ratio of 5:2:0.5:0.5 (see Example 6), and polyglyceryl-6 caprylate:polyglyceryl-10 diisostearate=weight ratio of 5:1 (see Example 7), and then heated to a temperature of about 60° C. and dissolved.

2) Purified water was added to each of the heated mixtures of 1), and the mixture was heated to a temperature of about 80° C. while stirring with a disperser; and 3) Each of the mixtures to which the purified water of 2) was added and heated was cooled to a temperature of normal temperature (about 25° C.) to prepare the cosmetic compositions of Examples 1 to 7.

TABLE 1

| Category | Material name | Example 1 | Example 2 | Example 3 | Example 4 | Example 5 | Example 6 | Example 7 |
|---|---|---|---|---|---|---|---|---|
| — | purified water | to 100 | to 100 | to 100 | to 100 | to 100 | to 100 | to 100 |
| water-soluble surfactant | polyglyceryl-6 caprylate | 5 | 7 | 0 | 2 | 5 | 5 | 5 |
|  | polyglyceryl-10 laurate | 2 | — | 7 | 5 | 2 | 2 | — |
| oil-soluble surfactant | polyglyceryl-10 diisostearate | 1 | 1 | 1 | 1 | — | 0.5 | 1 |
|  | polyglyceryl-10 dioleate) | — | — | — | — | 1 | 0.5 | — |

[Comparative Example 1]: Cosmetic Composition Containing Water-Soluble Surfactant and Oil-Soluble Surfactant A method of preparing a cosmetic composition according to Comparative Example 1 in Table 2 was as follows.

1) Polyglyceryl-6 caprylate and polyglyceryl-10 laurate as water-soluble surfactants, and polyglyceryl-10 diisostearate as oil-soluble surfactant were used, and mixed in a weight ratio of polyglyceryl-6 caprylate:polyglyceryl-10 laurate:polyglyceryl-10 diisostearate=5:2:0.05 to prepare a mixture, which was then heated to a temperature of about 60° C. and dissolved.

2) Purified water was added to the heated mixture of 1) and heated to a temperature of about 80° C. while stirring with a disperser.

3) The mixture to which the purified water of 2) was added and heated was cooled to a temperature of normal temperature (about 25° C.) to prepare a cosmetic composition.

[Comparative Example 2]: Cosmetic Composition Containing Water-Soluble Surfactant A method of preparing a cosmetic composition according to Comparative Example 2 in Table 2 was as follows.

1) Polyglyceryl-6 caprylate and polyglyceryl-10 laurate as water-soluble surfactants were used, and mixed in a weight ratio of polyglyceryl-6 caprylate:polyglyceryl-10 laurate=5:2 to prepare a mixture, which was then heated to a temperature of about 60° C. and dissolved.

2) Purified water was added to the heated mixture of 1) and heated to a temperature of about 80° C. while stirring with a disperser.

3) The mixture to which the purified water of 2) was added and heated was cooled to a temperature of normal temperature (about 25° C.) to prepare a cosmetic composition.

[Comparative Example 3]: Cosmetic Composition Containing Water-Soluble Surfactant and Oil-Soluble Surfactant A method of preparing a cosmetic composition according to Comparative Example 3 in Table 2 was as follows.

1) Polyglyceryl-10 laurate as a water-soluble surfactant and polyglyceryl-10 diisostearate as an oil-soluble surfactant were used, and mixed in a weight of polyglyceryl-10 laurate:polyglyceryl-10 diisostearate=2:1 to prepare a mixture, which was then heated to a temperature of about 60° C. and dissolved.

2) Purified water was added to the heated mixture of 1) and heated to a temperature of about 80° C. while stirring with a disperser.

3) The mixture to which the purified water of 2) was added and heated was cooled to a temperature of normal temperature (about 25° C.) to prepare a cosmetic composition.

[Comparative Example 4] Cosmetic Composition Containing Oil-Soluble Surfactant

A method of preparing a cosmetic composition according to Comparative Example 4 in Table 2 was as follows.

1) Polyglyceryl-10 diisostearate as an oil-soluble surfactant was heated to a temperature of about 60° C. and dissolved.

2) Purified water was added to the heated polyglyceryl-10 diisostearate of 1), and heated to a temperature of about 80° C. while stirring with a disperser.

3) The mixture to which the purified water of 2) was added and heated was cooled to a temperature of normal temperature (about 25° C.) to prepare a cosmetic composition.

[Test Example 1] Evaluation of Cleansing Power of Cosmetic Composition for Makeup Removal The cleansing power of the cosmetic compositions according to Examples 1 to 7 and Comparative Examples 1 to 4 prepared by varying the composition and content of the water-soluble surfactant and the oil-soluble surfactant was evaluated.

<Evaluation Method of Cleansing Power>

First, the makeup cosmetics for each of mascara, lipstick and foundation commonly used for cosmetic purposes were applied to white artificial leather at 0.02 g/20 μL each in an area of 2 cm×2 cm, and then dried for about 30 minutes. Then, the artificial leather to which the makeup cosmetic was applied was rubbed 5 times from top to bottom with a cotton pad (area: 3 cm×4 cm) dipped in 2 g of each of the cosmetic compositions of Examples 1 to 7 and Comparative Examples 1 to 4, and then removal effect (cleansing power) of makeup cosmetics applied to the artificial leather was checked with the naked eye and a color difference meter. Here, the color difference meter measures the brightness level (L) as a value of 5.00 to 99.99 AU (arbitrary unit), and when the brightness level is 70 AU or more (a level at which the cosmetic removal effect can be confirmed with the naked eye), it was evaluated that the cleansing effect of makeup cosmetics was high.

As a result,

1) When checking the cleansing effect with the naked eye, as shown in FIG. 1 below, ① It was confirmed that the cosmetic composition of Example 1 was excellent in cleansing effects of the three makeup cosmetics applied to artificial leather, namely foundation, lipstick and mascara; whereas ② It was confirmed that the cosmetic composition of Comparative Example 1 had only a cleansing effect for the mascara applied to artificial leather, and the cosmetic composition of Comparative Example 2 had almost no cleansing effect for foundation, lipstick and mascara applied to artificial leather.

In addition, when checking the cleansing effect with the naked eye, it was confirmed that the cosmetic compositions of Examples 2 to 7 exhibited a cleansing effect similar to that of the cosmetic composition of Example 1, that is, a cleansing effect for foundation, lipstick and mascara applied to artificial leather (the data not shown).

2) On the other hand, when checking the cleansing effect with a color difference meter, as shown in Table 3 and Table 4 below, ① The cosmetic compositions of Example 1, Example 2, Example 5, and Example 6 exhibited a brightness level of 70 AU or more in the artificial leather applied with three makeup cosmetics, namely foundation, lipstick and mascara, and thus, had very excellent cleansing effect;

② The cosmetic composition of Example 3, Example 4 and Example 7 exhibited a brightness level of 70 AU or more in two makeup cosmetics, that is, artificial leather applied with foundation and mascara, and thus had a relatively excellent cleansing effect;

③ It was confirmed that the cosmetic composition of Comparative Example 1 and Comparative Example 3 exhibited a brightness level of 70 AU or more only in the artificial leather applied with mascara, and thus had only a cleansing effect for mascara, and that the cosmetic composition of Comparative Example 4 exhibited a brightness level of 70 AU or more only in the artificial leather applied with foundation, and thus had only a cleansing effect for foundation;

④ It was confirmed that the cosmetic composition of Comparative Example 2 exhibited a brightness level of less than 70 AU in the artificial leather applied with foundation, lipstick and mascara, and thus, had almost no cleansing effect.

TABLE 3

| Formulation | Example 1 | Example 2 | Example 3 | Example 4 | Example 5 | Example 6 | Example 7 |
|---|---|---|---|---|---|---|---|
| foundation | 87.3 | 83.8 | 72.8 | 75.4 | 86.8 | 81.6 | 71.7 |
| lipstick | 76.9 | 70.3 | 58.3 | 68.5 | 71.0 | 74.6 | 60.4 |
| mascara | 84.2 | 83.0 | 78.8 | 80.9 | 84.8 | 83.3 | 71.3 |

TABLE 4

| Formulation | Comparative Example 1 | Comparative Example 2 | Comparative Example 3 | Comparative Example 4 |
|---|---|---|---|---|
| foundation | 64.2 | 65.3 | 62.8 | 71.1 |
| lipstick | 47.4 | 53.0 | 46.8 | 44.2 |
| mascara | 71.4 | 66.2 | 74.7 | 65.8 |

Consequently, as the content of the water-soluble surfactant in the cosmetic composition containing the water-soluble surfactant was increased, the cleansing power was improved, in particular, the cosmetic composition containing a mixture of a water-soluble surfactant having an HLB value of 13 or more and an oil-soluble surfactant having an HLB value of 12 or less in a weight ratio of 7:1 or 5:1 within the content range defined in one aspect of the present disclosure (Examples 1 to 7) confirmed that the makeup removal effect was remarkably increased.

[Test Example 2] Evaluation of Transparency of Cosmetic Composition for Makeup Removal The degree of transparency improvement of the cosmetic compositions according to Examples 1 to 7 and Comparative Examples 1 to 4 prepared by varying the composition and content of a water-soluble surfactant and an oil-soluble surfactant was evaluated by turbidity using a turbidimeter.

<Transparency Evaluation Method>

The transparency of the cosmetic compositions shown in Tables 1 and 2 was measured at a temperature of 22° C.±1° C. using an HF Scientific-Micro 1000IR Turbidimeter. Transparency was evaluated based on the turbidity measured by NTU (nephelometric turbidity unit), in which as the turbidity value is lower, the formulation is more transparent.

As a result, as shown in Tables 5 and 6 below, it was confirmed that:

① the cosmetic compositions of Examples 3 and 4 were very excellent in the turbidity reducing effect;
② the cosmetic compositions of Example 1, Example 2, Example 5, Example 6, and Example 7 were excellent in the turbidity reducing effect;
③ the cosmetic composition of Comparative Example 3 and Comparative Example 4 was very low in the turbidity reducing effect.

On the other hand, it was evaluated that the cosmetic composition of Comparative Example 2 containing no oil-soluble surfactant, and the cosmetic composition of Comparative Example 1 containing an oil-soluble surfactant in a low content (i.e., 0.05% by weight) showed a high effect of reducing turbidity, whereas each of the cosmetic compositions of Comparative Example 1 and Comparative Example 2 showed that the cleansing effect on the makeup cosmetic was not high as described in Test Example 1.

As a result, as the content of the water-soluble surfactant in the cosmetic composition containing an oil-soluble surfactant is increased, the transparency of the composition is improved according to the decrease in turbidity, in particular, the cosmetic composition containing a mixture of a water-soluble surfactant having an HLB value of 13 or more and an oil-soluble surfactant having an HLB value of 12 or less in a weight ratio of 7:1 or 5:1 within the content range defined in one aspect of the present disclosure confirmed that not only it had the effect of improving transparency due to a decrease in turbidity, but also the cleansing effect of makeup cosmetics was also significantly increased as described in Test Example 1.

TABLE 5

| | Example 1 | Example 2 | Example 3 | Example 4 | Example 5 | Example 6 | Example 7 |
|---|---|---|---|---|---|---|---|
| Turbidity (NTU) | 8.6 | 7.83 | 6.36 | 6.21 | 7.71 | 7.64 | 8.45 |

TABLE 6

| | Comparative Example 1 | Comparative Example 2 | Comparative Example 3 | Comparative Example 4 |
|---|---|---|---|---|
| Turbidity (NTU) | 10.5 | 6.91 | 207 | 357 |

Although specific parts of one aspect of the present invention have been described in detail, it will be apparent to those skilled in the art that these specific techniques are merely a preferred embodiment and that the scope of one aspect of the present invention is not limited thereto. Therefore, the substantial scope of one aspect of the present invention will be defined by the accompanying claims and their equivalents.

The invention claimed is:

1. A method of removing a makeup from skin of a subject, comprising applying to the skin upon which the makeup has already been applied, a composition, thereby removing the makeup from the skin,
   wherein said composition comprises, as an active ingredient, a mixture of a water-soluble surfactant having a (hydrophile-lipophile balance (HLB) value of 13 or more and an oil-soluble surfactant having an HLB value of 12 or less,
   wherein the water-soluble surfactant is one or more selected from the group consisting of polyglyceryl-6 caprylate, polyglyceryl-10 laurate, polyethylene glycol (PEG)-6 caprylic/capric glycerides, polysorbate 20, and disodium cocoamphodiacetate, and wherein the oil-soluble surfactant is one or more selected from the group consisting of polyglyceryl-10 diisostearate, polyglyceryl-2 laurate, polyglyceryl-2 sesquicaprylate, polyglyceryl-5 trioleate, polyglyceryl-10 dioleate, PEG-20 glyceryl triisostearate, PEG-8 isostearate, and PEG-8 glyceryl isostearate.

2. A method of improving the transparency of a cosmetic composition or a cosmetic product, comprising adding a mixture of a water-soluble surfactant having a (hydrophile-lipophile balance (HLB) value of 13 or more and an oil-soluble surfactant having an HLB value of 12 or less to the cosmetic composition or the cosmetic product,
wherein the water-soluble surfactant is one or more selected from the group consisting of polyglyceryl-6 caprylate, polyglyceryl-10 laurate, polyethylene glycol (PEG)-6 caprylic/capric glycerides, polysorbate 20, and disodium cocoamphodiacetate, and
wherein the oil-soluble surfactant is one or more selected from the group consisting of polyglyceryl-10 diisostearate, polyglyceryl-2 laurate, polyglyceryl-2 sesquicaprylate, polyglyceryl-5 trioleate, polyglyceryl-10 dioleate, PEG-20 glyceryl triisostearate, PEG-8 isostearate, and PEG-8 glyceryl isostearate.

3. The method according to claim 1, wherein the oil-soluble surfactant is one or more selected from the group consisting of polyglyceryl-10 diisostearate and polyglyceryl-10 dioleate.

4. The method according to claim 1, wherein the composition has a nephelometric turbidity unit (NTU) of 15 or less.

5. The method according to claim 1, wherein the mixture is a mixture of the water-soluble surfactant having a HLB value of 13 or more and the oil-soluble surfactant having an HLB value of 12 or less in a weight ratio of 3 to 20: 0.1 to 3.3.

6. The method according to claim 1, wherein the composition is formulated into a softening lotion, an astringent lotion, a nourishing lotion, a lotion, an eye cream, a nourishing cream, a massage cream, a cleansing cream, a cleansing foam, a cleansing water, a powder, an essence, or a facial mask pack.

7. The method according to claim 1, wherein the makeup is produced by applying to the skin one or more cosmetic formulations selected from the group consisting of a lipstick, a lip gloss, a lip balm, a lip pencil, a rouge, a lip palette, a pact, a powder, a blusher, a twin cake, a compact, a powder pact, a pressed powder, a skin cover, a foundation, a concealer, an eyeshadow, an eyebrow, an eyeliner, and a mascara.

8. The method according to claim 1, wherein the water-soluble surfactant is one or more selected from the group consisting of polyglyceryl-6 caprylate, and polyglyceryl-10 laurate.

\* \* \* \* \*